United States Patent
Chuang et al.

(10) Patent No.: US 7,368,053 B2
(45) Date of Patent: May 6, 2008

(54) MEMBRANE ZETA POTENTIAL MEASURING SYSTEM

(75) Inventors: Ching-Jung Chuang, Zhongli (TW); Yi-Chen Chiang, Tianzhong Town (TW); Hui-Ju Hsu, Lujhu Township, Taoyuan County (TW); Chia-Chun Wu, Xinzhuang (TW)

(73) Assignee: Chung Yuan Christian University, Chung-Li (TW)

(*) Notice: Subject to any disclaimer, the term of this patent is extended or adjusted under 35 U.S.C. 154(b) by 580 days.

(21) Appl. No.: 11/005,964

(22) Filed: Dec. 7, 2004

(65) Prior Publication Data
US 2005/0178702 A1   Aug. 18, 2005

(51) Int. Cl.
B01D 35/143 (2006.01)
G01N 27/60 (2006.01)

(52) U.S. Cl. .............................. 210/85; 210/90; 73/38; 324/439; 324/660

(58) Field of Classification Search ............. 73/861.08, 73/38; 204/627; 210/85, 90; 324/439, 660
See application file for complete search history.

(56) References Cited

U.S. PATENT DOCUMENTS
6,051,124 A * 4/2000 Aoki .......................... 204/600

FOREIGN PATENT DOCUMENTS
JP           63200052 A  *  8/1988

* cited by examiner

Primary Examiner—Terry K Cecil
(74) Attorney, Agent, or Firm—Rosenberg, Klein & Lee

(57) ABSTRACT

The present invention discloses a membrane zeta potential measuring system which comprises a first measuring course and a second measuring course. The provided system calculates the zeta potential of the membrane pores based on a first potential drop measured from the first measuring course, and calculates the zeta potential of the membrane surface based on a second potential drop measured from the second measuring course.

14 Claims, 17 Drawing Sheets

MEMBRANE ZETA POTENTIAL MEASURING SYSTEM

BACKGROUND OF THE INVENTION

1. Field of the Invention

The present invention is related to a membrane zeta potential measuring system, and more particularly to a measuring system which is able to measure both the membrane pore zeta potential and the membrane surface zeta potential.

2. Description of the Prior Art

Membrane separation is now a widely utilized technique in biotechnology, pharmaceutical and electronic industries for ultrafiltration operations. Fouling, a deposition on the membrane surface or in membrane pores, is the major problem in membrane separation processes resulting in a considerable reduction of the transmembrane permeability, a loss of valuable products and consequently an increase in operational costs.

Most membranes acquire an electric surface charge when brought into contact with an aqueous solution. The surface charge has been utilized as an important correlating parameter to study the fouling characteristics of ultrafiltration membranes with the greatest fouling typically seen under conditions where the solute and the membrane have opposite net charges. Zeta potential is an important and reliable indicator of this membrane surface charge, and knowledge of zeta potential is essential for the design and operation of membrane processes.

Currently, the most widely used tool for determining the zeta potential of membranes is the streaming potential. The streaming potential is generated when a fluid flows through a channel with a charged surface. In the charged channel, an electric double layer is formed at the phase boundary between the solid and liquid.

Streaming potential measurements can be performed in two different ways: by flow through membrane pores (transmembrane streaming potential) or by flow across the top surface of the membrane (tangential streaming flow).

In order to evaluate zeta potential from the streaming potential data, some important factors such as the overlap of electric double layers in the pore, the pore size distribution, and the detailed morphology and connectivity of the pore structure . . . etc., would need to be accounted for. Since these phenomena are largely unavailable, the data are mostly analyzed to obtain the "apparent zeta potential" by utilizing the Helmholtz-Smoluchowski equation or modified ones thereof.

Currently, commercial membranes for either research or industrial usages are often directly utilized based on the property information provided by the manufacturers; however, these provided membrane properties, especially the membrane charge herein, depend significantly on the physico-chemical properties of the solutions or suspensions contacted with the membrane.

Therefore, having a reliable measuring system to determine the membrane zeta potential under different conditions will provide useful information for the design and operation of a membrane system, and through which the operational costs will be greatly reduced.

SUMMARY OF THE INVENTION

Accordingly, the present invention provides a new membrane zeta potential measuring system to quickly and reliably determine the membrane zeta potential from the streaming potential data.

One object of the present invention is to provide a measuring system which is able to measure both the membrane pore zeta potential and the membrane surface zeta potential. The provided measuring system can comprise either two or three platforms. Furthermore, the present invention provides a simple sample-swapping procedure for performing the membrane surface and membrane pore zeta potential measurements. First, two parallel membranes are measured simultaneously to obtain the membrane surface zeta potential; afterwards, the membrane pore zeta potential measurement is carried out by simply replacing the original sample holder with another sample holder which has a bigger interspace. Thus, the present invention corresponds to both economic effect and utilization in industry.

Accordingly, the present invention discloses a membrane zeta potential measuring system which comprises a first measuring course to measure a first potential drop from which the zeta potential of the membrane pore can be evaluated; on the other hand, the provided measuring system comprises a second measuring course to measure a second membrane potential drop from which the zeta potential of the membrane surface can be evaluated.

DESCRIPTION OF THE PREFERRED EMBODIMENTS

What is probed into in the present invention is a membrane zeta potential measuring system. Preferred embodiments of the present invention will now be described in greater detail. Nevertheless, it should be recognized that the present invention can be practiced in a wide range of other embodiments besides those explicitly described, and the scope of the present invention is expressly not limited except as specified in the accompanying claims.

Referring to FIG. 1A, in a first embodiment of the present invention, there is provided a membrane zeta potential measuring system which comprises a first module, a second module, a first sample-holding module having a first channel; a first measuring course to measure the zeta potential of the membrane pore, a third module, a second sample-holding module having a second channel; a second measuring course to measure the potential of the membrane surface; and a voltmeter. The first module comprises a first route and a first detector wherein the first detector is used to measure the potential of the fluid in the first route and generate a first potential signal. The second module comprises a second route and a second detector wherein the second detector is used to measure the potential of the fluid in the second route and generates a second potential signal. The first sample-holding module is located between the first module and the second module and holds tight the membrane to be measured; more particularly, the first sample-holding module holds the membrane to be measured tight and places it in the first measuring course so the fluid can flow through the pores of the membrane to be measured. The first sample-holding module comprises at least one holding device, which may consist of an elastic material, to apply pressure onto the membrane to be measured and make it to abut on the first module; the at least one holding device further has a slot on it for the fluid to flow through. The first sample-holding module may further comprise an adjusting device to adjust the distance between the second module and the membrane to be measured so as to increase the fluid-containing space and uniform the internal pressure of the fluid.

In this embodiment, the first measuring course is formed by the first route, the first channel and the second route. The second sample-holding module is located between the first module and the third module and holds tight two parallel membranes that are to be measured; more particularly, the second sample-holding module holds tight the two parallel membranes in the second measuring course so the fluid can flow through the interspace between the two parallel membranes. The second sample-holding module comprises at least one holding device, which may consist of an elastic material, to apply pressure onto the two parallel membranes that are to be measured and make them to abut on the first module and the third module; the at least one holding device further has a slot on it for the fluid to flow through. The sample-holding module may further comprise at least one adjusting device to adjust the distance between the two parallel membranes that are to be measured. The third module comprises a third detector and a fourth detector wherein the third detector is used to measure the potential of the fluid at the inlet of the second channel and generate a third potential signal; and the fourth detector is used to measure the potential of the fluid at the outlet of the second channel and generate a fourth potential signal. Finally, the voltmeter receives the first and the second potential signals and calculates a first potential drop from which the zeta potential of the membrane pore is then evaluated; on the other hand, the voltmeter receives the third and the fourth potential signals and calculates a second potential drop from which the zeta potential of the membrane surface is then evaluated.

Referring to FIG. 1B, in the above embodiment, the first measuring course comprises: a first conduit in the first route to lead the fluid into the membrane zeta potential measuring system; a first path in the first channel to receive the fluid from the first conduit; a second conduit in the second route to receive the fluid from the first path; a first fluid-containing space in the second route to receive the fluid from the second conduit and keep it for a while; a second path in the first channel to receive the fluid from the first fluid-containing space and lead it into the membrane pores; a second fluid-containing space in the first route to receive the fluid from the membrane pores, wherein a porous board may be placed in the second fluid-containing space to support the membrane to be measured; and a third conduit in the first route to receive the fluid from the second fluid-containing space and lead it out of the membrane zeta potential measuring system. In addition, as illustrated in FIG. 1C, the second measuring course comprises: a first conduit in the first route to lead the fluid into the membrane zeta potential measuring system; the second channel to receive the fluid from the first conduit and lead it into the interspace of two parallel membranes that are to be measured; and a fourth conduit in the first route to receive the fluid from the interspace of the two parallel membranes and lead it out of the membrane zeta potential measuring system. The membrane zeta potential measuring system may further comprise a pressure detector to measure the internal pressure of the fluid in the second route of the first measuring course and the fluid at the inlet of the second channel of the second measuring course, respectively.

Referring to FIG. 2, in a second embodiment of the present invention, there is provided a membrane zeta potential measuring system which comprises a feeding module, a conductivity detector, a membrane zeta potential measuring module, a circulation module, a first control valve, a second control valve, a pressure detector and a central processing module. The conductivity detector is used to detect the conductivity of the fluid and generate a conductivity signal. The membrane zeta potential measuring module comprises a first apparatus, a second apparatus and a third apparatus wherein the first apparatus and the second apparatus together form a first measuring course via which the membrane zeta potential measuring module receives the fluid from the feeding module and generate a first potential signal; the first apparatus and the third apparatus together form a second measuring course via which the membrane zeta potential measuring module receives the fluid from the feeding module and generate a second potential signal. The circulation module is used to drive the fluid circulation among the feeding module and the membrane zeta potential measuring module. The circulation module may comprise a pump for driving force of the fluid circulation. In addition, the circulation module may comprise a feedback control valve to lead part of the fluid that is outside the feeding module back to the feeding module; the internal pressure of the fluid can be adjusted by the feedback control valve, too. The first control valve leads the fluid in the first measuring course to the circulation module; and the second control valve leads the fluid in the second measuring course to the circulation module. Afterwards, the pressure detector measures the internal pressure of the fluid in the first measuring course and the second measuring course and generates a first pressure signal and a second pressure signal, respectively. Then, the zeta potential of the membrane pore is evaluated by the central processing module based on the conductivity signal, the first pressure signal and the first potential signal; similarly, the zeta potential of the membrane surface is evaluated by the central processing module based on the conductivity signal, the second pressure signal and the second potential signal. On the other hand, the membrane zeta potential measuring system may further comprise a buffer cell located between the feeding module and the membrane zeta potential measuring module for lowering fluctuation of the fluid pressure; the buffer cell leads the fluid into the first measuring course and the second measuring course. The provided membrane zeta potential measuring system may further comprise a PH meter to measure the PH value of the fluid.

In this embodiment, the membrane zeta potential measuring module comprises a first apparatus, a second apparatus, a first sample-holding apparatus having a first channel; a first measuring course to measure the zeta potential of the membrane pore, a third apparatus, a second sample-holding apparatus having a second channel; a second measuring course to measure the potential of the membrane surface; and a voltmeter. The first apparatus comprises a first route and a first detector wherein the first detector is used to measure the potential of the fluid in the first route and generate a first potential signal. The second apparatus comprises a second route and a second detector wherein the second detector is used to measure the potential of the fluid in the second route and generate a second potential signal. The first sample-holding apparatus is located between the first apparatus and the second apparatus and holds tight the membrane to be measured; more particularly, the first sample-holding apparatus holds the membrane to be measured tight and places it in the first measuring course so the fluid can flow through the pores of the membrane to be measured. The first sample-holding apparatus comprises at least one holding device, which may consist of an elastic material, to apply pressure onto the membrane to be measured and make it to abut on the first apparatus; the at least one holding device further has a slot on it for the fluid to flow through. The first sample-holding apparatus may further comprise an adjusting device to adjust the distance between the second apparatus and the membrane to be measured so as to increase the fluid-containing space and uniform the internal pressure of the fluid.

On the other hand, the second sample-holding apparatus is located between the first apparatus and the third apparatus and holds tight two parallel membranes that are to be measured; more particularly, the second sample-holding apparatus holds tight the two parallel membranes in the second measuring course so the fluid can flow through the interspace between the two parallel membranes. The second sample-holding module comprises at least one holding device, which may consist of an elastic material, to apply pressure onto the two parallel membranes and make them to abut on the first apparatus and the third apparatus; the at least one holding device further has a slot on it for the fluid to flow through. The second sample-holding apparatus may further comprise at least one adjusting device to adjust the distance between the two parallel membranes that are to be measured. The second measuring course is formed by the first route and the second channel. The third apparatus comprises a third detector and a fourth detector wherein the third detector is used to measure the potential of the fluid at the inlet of the second channel and generate a third potential signal; and the fourth detector is used to measure the potential of the fluid at the outlet of the second channel and generate a fourth potential signal. Finally, the voltmeter receives the first and the second potential signals and calculates a first potential drop from which the zeta potential of the membrane pore is then evaluated; on the other hand, the voltmeter receives the third and the fourth potential signals and calculates a second potential drop from which the zeta potential of the membrane surface is then evaluated.

In this embodiment, the first measuring course comprises: a first conduit in the first route to lead the fluid into the membrane zeta potential measuring module; a first path in the first channel to receive the fluid from the first conduit; a second conduit in the second route to receive the fluid from the first path; a first fluid-containing space in the second route to receive the fluid from the second conduit and keep it for a while so the pressure detector can measure the internal pressure of the fluid in the second route and generate a first pressure signal; a second path in the first channel to receive the fluid from the first fluid-containing space so the fluid in the second path can flow into the membrane pores; a second fluid-containing space in the first route to receive the fluid from the membrane pores, wherein a porous board may be placed in the second fluid-containing space to support the membrane to be measured; and a third conduit in the first route to receive the fluid from the second fluid-containing space and lead it out of the membrane zeta potential measuring module. The first control valve controls the fluid in the third conduit in order to lead the fluid from the first measuring course to the circulation module. On the other hand, the second measuring course comprises: a first conduit in the first route to lead the fluid into the membrane potential measuring module; the second channel to receive the fluid from the first conduit and lead it into the interspace of the two parallel membranes that are to be measured, wherein the pressure detector measures the internal pressure of the fluid at the inlet of the second channel and generates a second pressure signal; and a fourth conduit in the first route to receive the fluid from the interspace of the two parallel membranes and lead it out of the membrane zeta potential measuring module, wherein the second control valve controls the fluid from the fourth conduit in order to lead the fluid from the second measuring course to the circulation module.

Referring to FIGS. 3A, 3B and 3C, in a third embodiment of the present invention, there is provided a membrane zeta potential measuring apparatus which comprises: a first platform 31, a second platform 32, a first sample-holding element 34 having a first path 3410 and a second path 3420; a first measuring course to measure the zeta potential of the membrane pore; a third platform 33, a second sample-holding element 35 having a third path 3510; a second measuring course to measure the zeta potential of the membrane surface; and a voltmeter. The first platform 31 comprises: a first conduit 3130 to lead in the fluid; a first fluid-containing space 3140, a second conduit 3150, a third conduit 3160, and a first detector 3120$a$. One end of the third conduit 3160 is connected with the first fluid-containing space 3140; the first detector 3120$a$ measures the potential of the fluid in the first fluid-containing space 3140 and generates a first potential signal. The first platform 31 further comprises a first detecting tunnel 3120$b$ to place the first detector 3120$a$; one end of the first detecting tunnel 3120$b$ is connected with the first fluid-containing space 3140. The second platform 32 comprises: a fourth conduit 3220, a second fluid-containing space 3230, and a second detector 3210$a$. One end of the fourth conduit 3220 is connected with the second fluid-containing space 3230; the second detector 3210$a$ measures the potential of the fluid in the second fluid-containing space 3230 and generates a second potential signal. The second platform 32 further comprises a second detecting tunnel 3210$b$ to place the second detector 3210$a$; one end of the second detecting tunnel 3210$b$ is connected with the second fluid-containing space 3230. The first sample-holding element 34 is located between the first platform 31 and the second platform 32 and holds tight the membrane to be measured. One end of the first path 3410 is connected with the first conduit 3130; one end of the second path 3420 is connected with the first fluid-containing space 3140, and the other end of the second path 3420 is connected with the second fluid-containing space 3230. The first sample-holding element 34 may further comprise a fourth path 3430 which is connected with the second path 3420.

In this embodiment, the first measuring course is formed by the first platform 31, the first sample-holding element 34 and the second platform 32. The third platform 33 comprises a third detector 3310$a$, a fourth detector 3320$a$, a third detecting tunnel 3310$b$ to place the third detector 3310$a$; and a fourth detecting tunnel 3320$b$ to place the fourth detector 3320$a$. One end of the third detecting tunnel 3310$b$ and one end of the fourth detecting tunnel 3320$b$ are connected with the third path 3510, respectively. The second sample-holding element 35 is located between the first platform 31 and the third platform 33 and holds tight two parallel membranes that are to be measured. One end of the third path 3510 is connected with the first conduit 3130, the first fluid-containing space 3140 and the second conduit 3150; the other end of the third path 3510 is connected with the third detector 3310$a$ and the fourth detector 3320$a$. The second measuring course is formed by the first platform 31, the second sample-holding element 35 and the third platform 33. The third detector 3310$a$ measures the potential of the fluid at the inlet of the third path 3510 and generates a third potential signal; the fourth detector 3320$a$ measures the potential of the fluid at the outlet of the third path 3510 and generates a fourth potential signal. The voltmeter receives the first and the second potential signals and calculates a first potential drop from which the zeta potential of the membrane pore is then evaluated; on the other hand, the voltmeter receives the third and the fourth potential signals and calculates a second potential drop from which the zeta potential of the membrane surface is then evaluated.

Additionally, the second conduit 3150 and the third conduit 3160 are used to lead the fluid out of the membrane zeta potential measuring apparatus. On the other hand, the first platform 31 further comprises a pressure detecting tunnel 3110*b* in which a pressure detector 3110*a* is placed; one end of the pressure detecting tunnel 3110*b* is connected with the fourth path 3430 and the third path 3510 so the pressure detector 3110*a* can measure the internal pressure of the fluid in the second fluid-containing space 3230 and the third path 3510.

Referring to FIGS. 4A, 4B and 4C, in a fourth embodiment of the present invention, there is provided a membrane zeta potential measuring apparatus which comprises: a first platform 41, a second platform 42, a first sample-holding element 44 having a first path 4410; a first measuring course to measure the zeta potential of the membrane pore; a third platform 43, a second sample-holding element 45 having a second path 4510; a second measuring course to measure the zeta potential of the membrane surface, and a voltmeter. The first platform 41 comprises a first fluid-containing space 4130, a first conduit 4140, a second conduit 4150, and a first detector 4120*a*. One end of the second conduit 4150 is connected with the first fluid-containing space 4130; the first detector 4120*a* measures the potential of the fluid in the first fluid-containing space 4130 and generates a first potential signal. The first platform 41 further comprises a first detecting tunnel 4120*b* to place the first detector 4120*a*; one end of the first detecting tunnel 4120*b* is connected with the first fluid-containing space 4130. The second platform 42 comprises a third conduit 4220 to lead in the fluid, a second fluid-containing space 4230, and a second detector 4210*a*, wherein one end of the third conduit 4220 is connected with the second fluid-containing space 4230; the second detector 4210*a* measures the potential of the fluid in the second fluid-containing space 4230 and generates a second potential signal. The second platform 42 further comprises a second detecting tunnel 4210*b* to place the second detector 4210*a*; one end of the second detecting tunnel 4210*b* is connected with the second fluid-containing space 4230. The first sample-holding element 44 is located between the first platform 41 and the second platform 42 and holds tight the membrane to be measured. One end of the first path 4410 is connected with the first fluid-containing space 4130; the other end of the first path 4410 is connected with the second fluid-containing space 4230.

In this embodiment, the first measuring course is formed by the first platform 41, the first sample-holding element 44 and the second platform 42. On the other hand, the third platform 43 comprises a fourth conduit 4330 to lead in the fluid; a third detector 4310*a*, and a fourth detector 4320*a*. The second sample-holding element 45 is located between the first platform 41 and the third platform 43 and holds tight two parallel membranes that are to be measured. One end of the second path 4510 is connected with the first fluid-containing space 4130 and the first conduit 4140; the other end of the second path 4510 is connected with the fourth conduit 4330, the third detector 4310*a* and the fourth detector 4320*a*. The third platform 43 further comprises a third detecting tunnel 4310*b* to place the third detector 4310*a*; and a fourth detecting tunnel 4320*b* to place the fourth detector 4320*a*. One end of the third detecting tunnel 4310*b* and one end of the fourth detecting tunnel 4320*b* are connected with the second path 4510, respectively. The second measuring course is formed by the first platform 41, the second sample-holding element 45 and the third platform 43. The third detector 4310*a* measures the potential of the fluid at the inlet of the second path 4510 and generates a third potential signal; the fourth detector 4320*a* measures the potential of the fluid at the outlet of the second path 4510 and generates a fourth potential signal. The voltmeter receives the first and the second potential signals and calculates a first potential drop from which the zeta potential of the membrane pore is then evaluated; on the other hand, the voltmeter receives the third and the fourth potential signals and calculates a second potential drop from which the zeta potential of the membrane surface is then evaluated.

Additionally, the first conduit 4140 and the second conduit 4150 are used to lead the fluid out of the membrane zeta potential measuring apparatus. On the other hand, the first platform 41 further comprises a pressure detecting tunnel 4110*b* in which a pressure detector 4110*a* is placed; one end of the pressure detecting tunnel 4110*b* is connected with the first path 4410 and the second path 4510 so the pressure detector 4110*a* can measure the internal pressure of the fluid in the second fluid-containing space 4230 and the second path 4510.

Referring to FIG. 5A, in a fifth embodiment of the present invention, there is provided a membrane zeta potential measuring system which comprises a first module, a second module, a sample-holding module having a channel; a first measuring course to measure the zeta potential of the membrane pore; a second measuring course to measure the potential of the membrane surface; and a voltmeter. The first module comprises a first route and a first detector wherein the first detector is used to measure the potential of the fluid in the first route and generate a first potential signal. The second module comprises a second route, a second detector and a third detector. The sample-holding module is located between the first module and the second module and holds tight the membrane to be measured. When measuring the potential of the membrane pore, the sample-holding module holds tight the membrane to be measured and places it in the first measuring course so the fluid can flow into the pores of the membrane to be measured. The sample-holding module comprises at least one holding device, which may consist of an elastic material, to apply pressure onto the membrane to be measured and make it to abut on the first module; the at least one holding device further has a slot on it for the fluid to flow through. The sample-holding module may further comprise an adjusting device to adjust the distance between the second module and the membrane to be measured so as to increase the fluid-containing space and uniform the internal pressure of the fluid.

When measuring the potential of the membrane surface, the sample-holding module holds tight two parallel membranes that are to be measured and places them in the second measuring course so the fluid can flow into the interspace of the two parallel membranes. The sample-holding module comprises at least one holding device to apply pressure onto the two parallel membranes and make them to abut on the first module and the second module; the at least one holding device further has a slot on it for the fluid to flow through. The sample-holding module may further comprise an adjusting device to adjust the distance between the two parallel membranes that are to be measured.

In this embodiment, the first measuring course is formed by the first route, the channel and the second route. The second and/or the third detector measures the potential of the fluid in the channel of the first measuring course and generates a second potential signal. On the other hand, the second measuring course is formed by the first route and the channel, wherein the second detector measures the potential of the fluid at the inlet of the channel and generates a third potential signal, and the third detector measures the potential of the fluid at the outlet of the channel and generates a fourth potential signal. Finally, the voltmeter receives the first and the second potential signals and calculates a first potential drop from which the zeta potential of the membrane pore is then evaluated; on the other hand, the voltmeter receives the third and the fourth potential signals and calculates a second potential drop from which the zeta potential of the membrane surface is then evaluated.

Referring to FIG. 5B, in the above embodiment, the first measuring course comprises: a first conduit in the second route to lead the fluid into the membrane zeta potential measuring system; the channel to receive the fluid from the first conduit and keep it for a while so the fluid can flow into the pores of the membrane to be measured; a fluid-containing space in the first route to receive the fluid from the membrane pores, wherein a porous board may be placed in the fluid-containing space to support the membrane to be measured; and a second conduit in the first route to receive the fluid from the fluid-containing space and lead it out of the membrane zeta potential measuring system. In addition, as illustrated in FIG. 5C, the second measuring course comprises: a first conduit in the second route to lead the fluid into the membrane zeta potential measuring system; the channel to receive the fluid from the first conduit and lead it into the interspace of the two parallel membranes that are to be measured; and a third conduit in the second route to receive the fluid from the interspace of the two parallel membranes and lead it out of the membrane zeta potential measuring system. The membrane zeta potential measuring system may further comprise a pressure detector to measure the internal pressure of the fluid in the channel of the first measuring course and the fluid in the channel of the second measuring course, respectively.

Referring to FIG. 6, in a sixth embodiment of the present invention, there is provided a membrane zeta potential measuring system which comprises a feeding module, a conductivity detector, a membrane zeta potential measuring module having a first measuring course and a second measuring course, a circulation module, a first control valve, a second control valve, a pressure detector, and a central processing module. The conductivity detector is used to detect the conductivity of the fluid and generate a conductivity signal. The membrane zeta potential measuring module receives the fluid from the feeding module via the first measuring course and generates a first potential signal; similarly, the membrane zeta potential measuring module receives the fluid from the feeding module via the second measuring course and generates a second potential signal. The circulation module is used to drive the circulation of fluid among the feeding module and the membrane zeta potential measuring module. The circulation module may comprise a pump for driving force of the fluid circulation. In addition, the circulation module may comprise a feedback control valve to lead part of the fluid that is outside the feeding module back to the feeding module; the internal pressure of the fluid can be adjusted by the feedback control valve, too. The first control valve leads the fluid in the first measuring course to the circulation module; the second control valve leads the fluid in the second measuring course to the circulation module. Afterwards, the pressure detector measures the internal pressure of the fluid in the first measuring course and the second measuring course and generates a first pressure signal and a second pressure signal, respectively. Then, the zeta potential of the membrane pore is evaluated by the central processing module based on the conductivity signal, the first pressure signal and the first potential signal; similarly, the zeta potential of the membrane surface is evaluated by the central processing module based on the conductivity signal, the second pressure signal and the second potential signal. On the other hand, the membrane zeta potential measuring system may further comprise a buffer cell located between the feeding module and the membrane zeta potential measuring module for lowering fluctuation of the fluid pressure; the buffer cell leads the fluid into the first measuring course and the second measuring course. When measuring the potential of the membrane pore, the central processing module sends a complementary control signal to open the first control valve and close the second control valve, through which to enable the first measuring course and disable the second measuring course. When measuring the potential of the membrane surface, the central processing module sends a complementary control signal to close the first control valve and open the second control valve, through which to enable the second measuring course and disable the first measuring course.

In this embodiment, the membrane zeta potential measuring module comprises a first apparatus, a second apparatus, a sample-holding apparatus having a channel; a first measuring course to measure the zeta potential of the membrane pore; a second measuring course to measure the potential of the membrane surface; and a voltmeter. The first apparatus comprises a first route and a first detector wherein the first detector is used to measure the potential of the fluid in the first route and generate a first potential signal. The second apparatus comprises a second route, a second detector and a third detector. The sample-holding apparatus is located between the first apparatus and the second apparatus and holds tight the membrane to be measured. When measuring the potential of the membrane pore, the sample-holding apparatus holds tight the membrane to be measured and places it in the first measuring course so the fluid can flow into the pores of the membrane to be measured. The sample-holding apparatus comprises at least one holding device, which may consist of an elastic material, to apply pressure onto the membrane to be measured and make it to abut on the first apparatus; the at least one holding device further has a slot on it for the fluid to flow through. The sample-holding apparatus may further comprise an adjusting device to adjust the distance between the second apparatus and the membrane to be measured so as to increase the fluid-containing space and uniform the internal pressure of the fluid.

When measuring the potential of the membrane surface, the sample-holding apparatus holds tight two parallel membranes that are to be measured and places them in the second measuring course so the fluid can flow into the interspace of the two parallel membranes. The sample-holding apparatus comprises at least one holding device, which may consist of an elastic material, to apply pressure onto the two parallel membranes and make them to abut on the first apparatus and the second apparatus; the at least one holding device further has a slot on it for the fluid to flow through. The sample-holding apparatus may further comprise at least one adjusting device to adjust the distance between the two parallel membranes that are to be measured.

In this embodiment, the first measuring course is formed by the first route, the channel and the second route. The second and/or the third detector measures the potential of the fluid in the channel and generates a second potential signal.

On the other hand, the second measuring course is formed by the first route and the channel, wherein the second detector measures the potential of the fluid at the inlet of the channel and generates a third potential signal; and the third detector measures the potential of the fluid at the outlet of the channel and generates a fourth potential signal. Finally, the voltmeter receives the first and the second potential signals and calculates a first potential drop from which the zeta potential of the membrane pore is then evaluated; on the other hand, the voltmeter receives the third and the fourth potential signals and calculates a second potential drop from which the zeta potential of the membrane surface is then evaluated.

In this embodiment, the first measuring course comprises: a first conduit in the second route to lead the fluid into the membrane zeta potential measuring module; the channel to receive the fluid from the first conduit and keep it for a while so the fluid can flow through the membrane pores; a fluid-containing space in the first route to receive the fluid from the membrane pores, wherein a porous board may be placed in the fluid-containing space to support the membrane to be measured; and a second conduit in the first route to receive the fluid from the fluid-containing space and lead it out of the membrane zeta potential measuring module. The first control valve controls the fluid in the second conduit to lead the fluid in the first measuring course to the circulation module. On the other hand, the second measuring course comprises: a first conduit in the second route to lead the fluid into the membrane zeta potential measuring module; the channel to receive the fluid from the first conduit and lead it into the interspace of two parallel membranes that are to be measured, wherein the pressure detector detects the internal pressure of the fluid at the inlet of the channel and generates a second pressure signal; and a third conduit in the second route to receive the fluid from the interspace of the two parallel membranes and lead it out of the membrane zeta potential measuring module. The second control valve controls the fluid in the third conduit to lead the fluid in the second measuring course to the circulation module. The membrane zeta potential measuring module may further comprise a pressure detector to measure the internal pressure of the fluid in the channel of the first measuring course and the fluid in the channel of the second measuring course, respectively.

Referring to FIGS. 7A and 7B, in a seventh embodiment of the present invention, there is provided a membrane zeta potential measuring apparatus which comprises: a first platform 71, a second platform 72, a sample-holding element 73 having a channel 7310; a first measuring course to measure the zeta potential of the membrane pore; a second measuring course to measure the zeta potential of the membrane surface, and a voltmeter. The first platform 71 comprises a fluid-containing space 7130, a first conduit 7140 and a first detector 7120a. One end of the first conduit 7140 is connected with the fluid-containing space 7130; the first detector 7120a measures the potential of the fluid in the fluid-containing space 7130 and generates a first potential signal. The first platform 71 further comprises a first detecting tunnel 7120b to place the first detector 7120a; one end of the first detecting tunnel 7120b is connected with the fluid-containing space 7130. The second platform 72 comprises a second conduit 7230 to lead in the fluid, a third conduit 7240, a second detector 7210a and a third detector 7220a. The second platform 72 further comprises a second detecting tunnel 7210b to place the second detector 7210a, and a third detecting tunnel 7220b to place the third detector 7220a; one end of the second detecting tunnel 7210b and the third detecting tunnel 7220b are connected with the channel 7310, respectively.

In this embodiment, the sample-holding element 73 is located between the first platform 71 and the second platform 72 and holds tight a membrane to be measured 74. One end of the channel 7310 is connected with the fluid-containing space 7130 and the other end of the channel 7310 is connected with the second conduit 7230 and the third conduit 7240. The first platform 71, the sample-holding element 73 and the second platform 72 together form a first measuring course for the membrane pore potential measurement and a second measuring course for the membrane surface potential measurement: the second detector 7210a and/or the third detector 7220a measures the potential of the fluid in the channel 7310 of the first measuring course and generates a second potential signal; the second detector 7210a measures the potential of the fluid at the inlet of the channel 7310 and generates a third potential signal; the third detector 7220a measures the potential of the fluid at the outlet of the channel 7310 and generates a fourth potential signal; finally, the voltmeter receives the first and the second potential signals and calculates a first potential drop from which the zeta potential of the membrane pore is then evaluated; on the other hand, the voltmeter receives the third and the fourth potential signals and calculates a second potential drop from which the zeta potential of the membrane surface is then evaluated.

Additionally, the first platform 71 may further comprise a pressure detecting tunnel 7110b in which a pressure detector 7110a is placed; one end of the pressure detecting tunnel 7110b is connected with the channel 7130 so the pressure detector 7110a can measure the internal pressure of the fluid in the channel 7310 of the first measuring course and the second measuring course, respectively. The first conduit 7140 and the third conduit 7240 are used to lead the fluid out of the membrane zeta potential measuring apparatus.

Accordingly, the present invention provides a new membrane zeta potential measuring system which can comprise either two or three platforms. Furthermore, the present invention provides a simple sample-swapping procedure for performing the membrane surface and membrane pore zeta potential measurements. First, two parallel membranes are measured simultaneously to obtain the membrane surface zeta potential; afterwards, the membrane pore potential measurement is carried out by simply replacing the original sample-holding module with another sample holder which has a bigger interspace. Thus, the present invention corresponds to both economic effect and utilization in industry.

The present invention discloses a membrane zeta potential measuring system which comprises a first measuring course to measure a first potential drop from which the zeta potential of the membrane pore is evaluated; a second measuring course to measure a second membrane potential drop from which the zeta potential of the membrane surface is evaluated.

Obviously, many modifications and variations of the present invention are possible in light of the above teachings. It is therefore to be understood that within the scope of the appended claims, the present invention may be practiced otherwise than as specifically described herein. Although specific embodiments have been illustrated and described, it will be obvious to those skilled in the art that various modifications may be made without departing from what is intended to be limited solely by the appended claims.

Figure 1A:
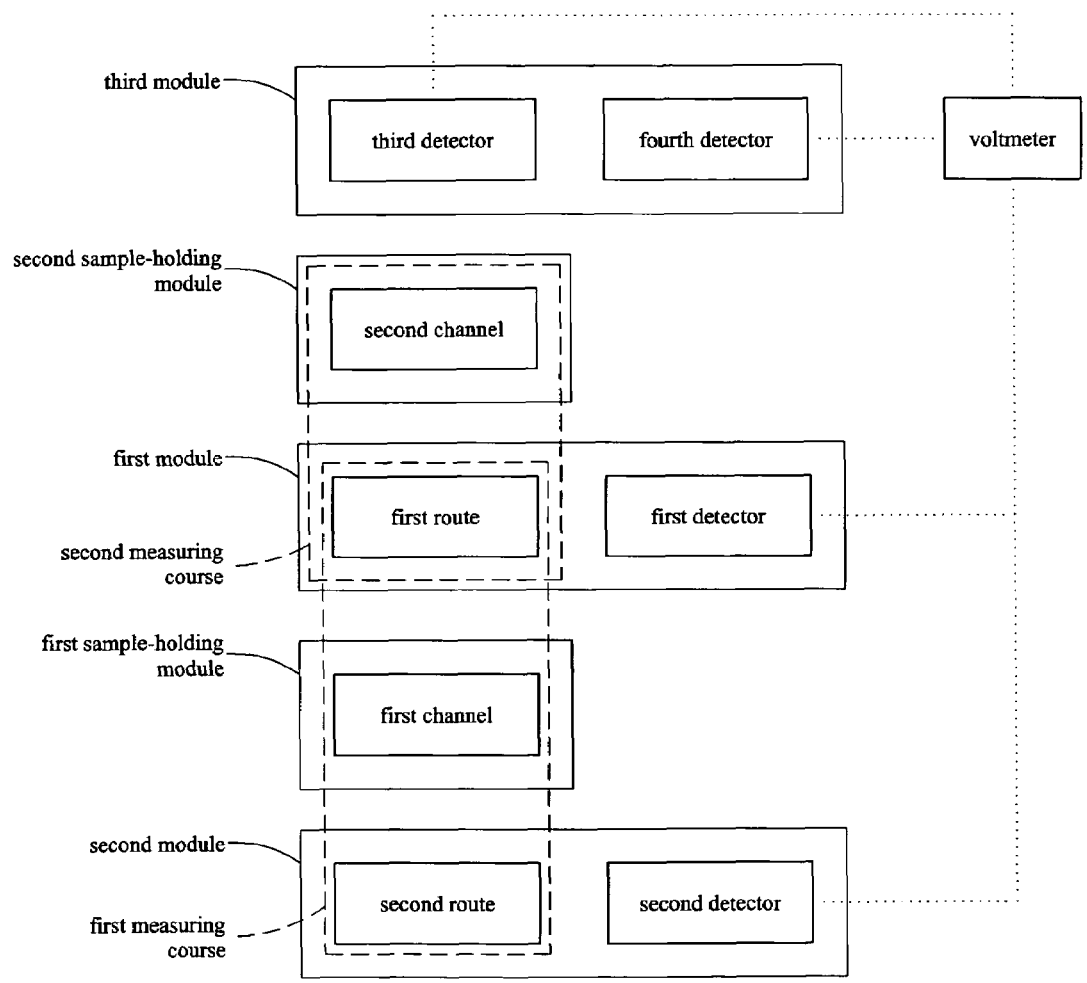
FIG. 1A is a block diagram illustrating a membrane zeta potential measuring system in accordance with a first preferred embodiment of the present invention.
Figure 1B:
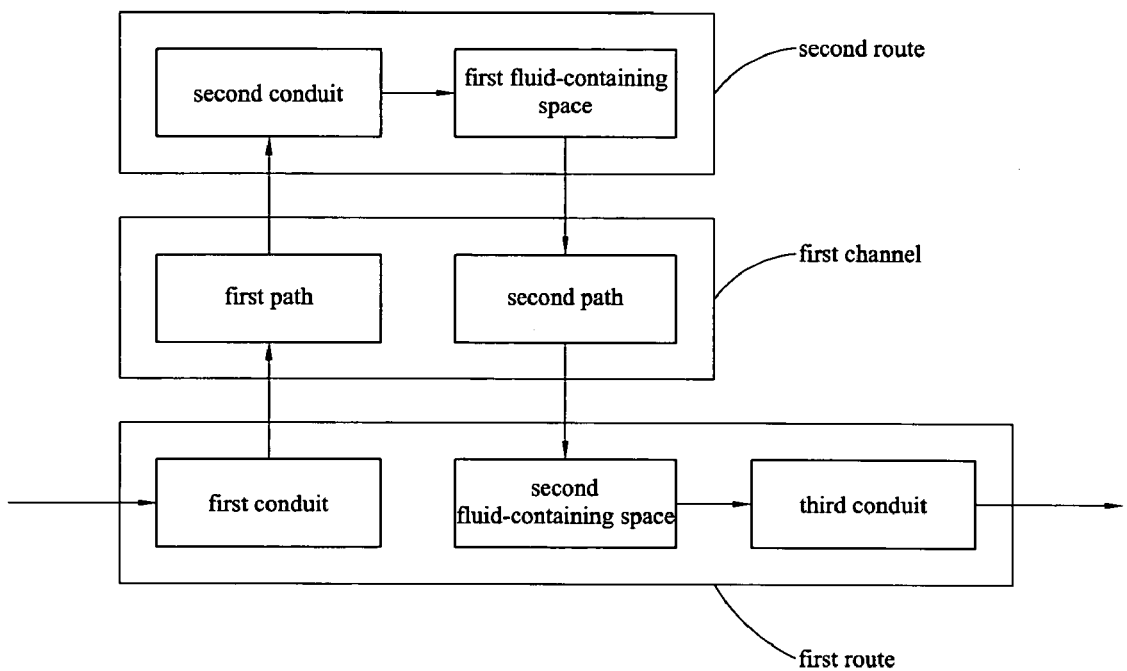
FIG. 1B is a block diagram illustrating the first measuring course of the membrane zeta potential measuring system in accordance with the first preferred embodiment of the present invention.
Figure 1C:
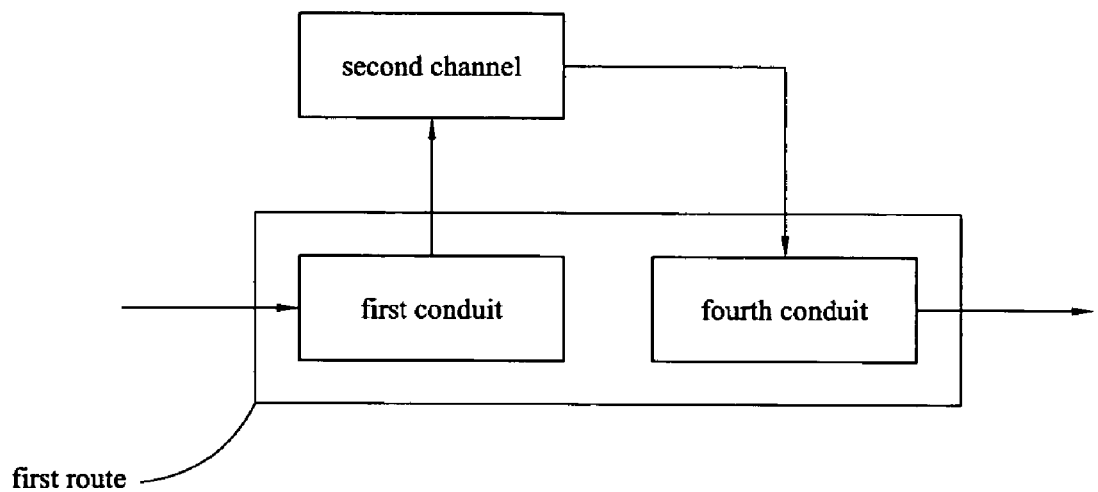
FIG. 1C is a block diagram illustrating the second measuring course of the membrane zeta potential measuring system in accordance with the first preferred embodiment of the present invention.
Figure 2:
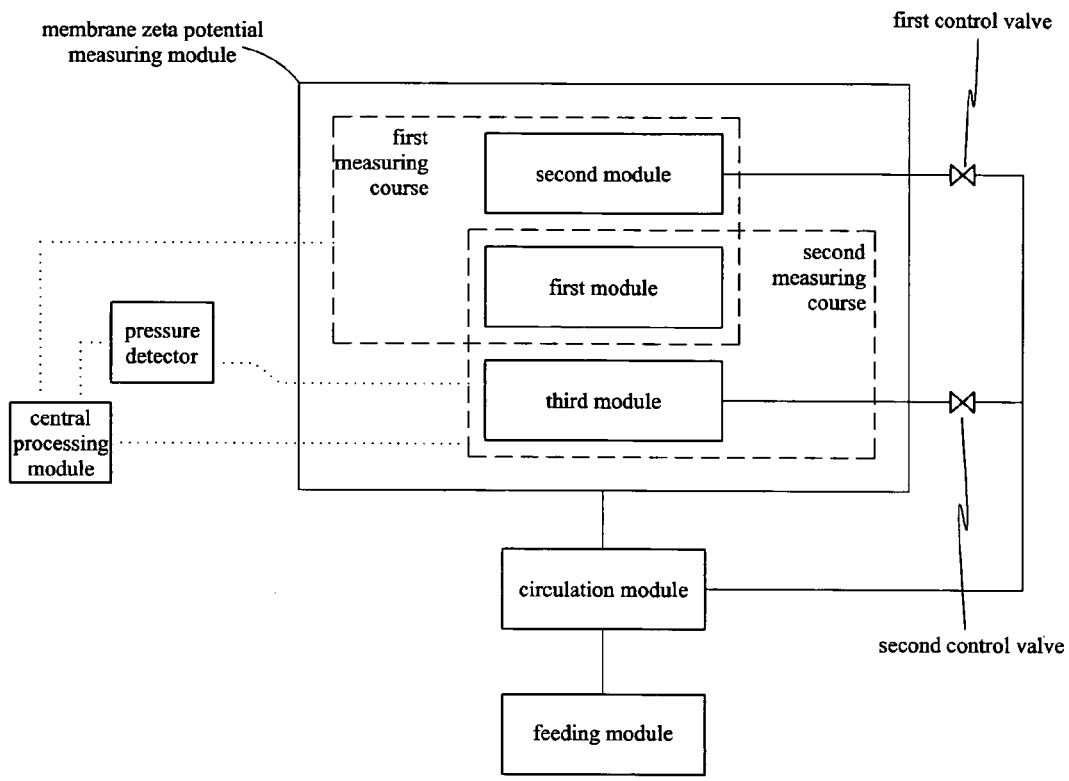
FIG. 2 is a block diagram illustrating a membrane zeta potential measuring system in accordance with a second preferred embodiment of the present invention.
Figure 3A:
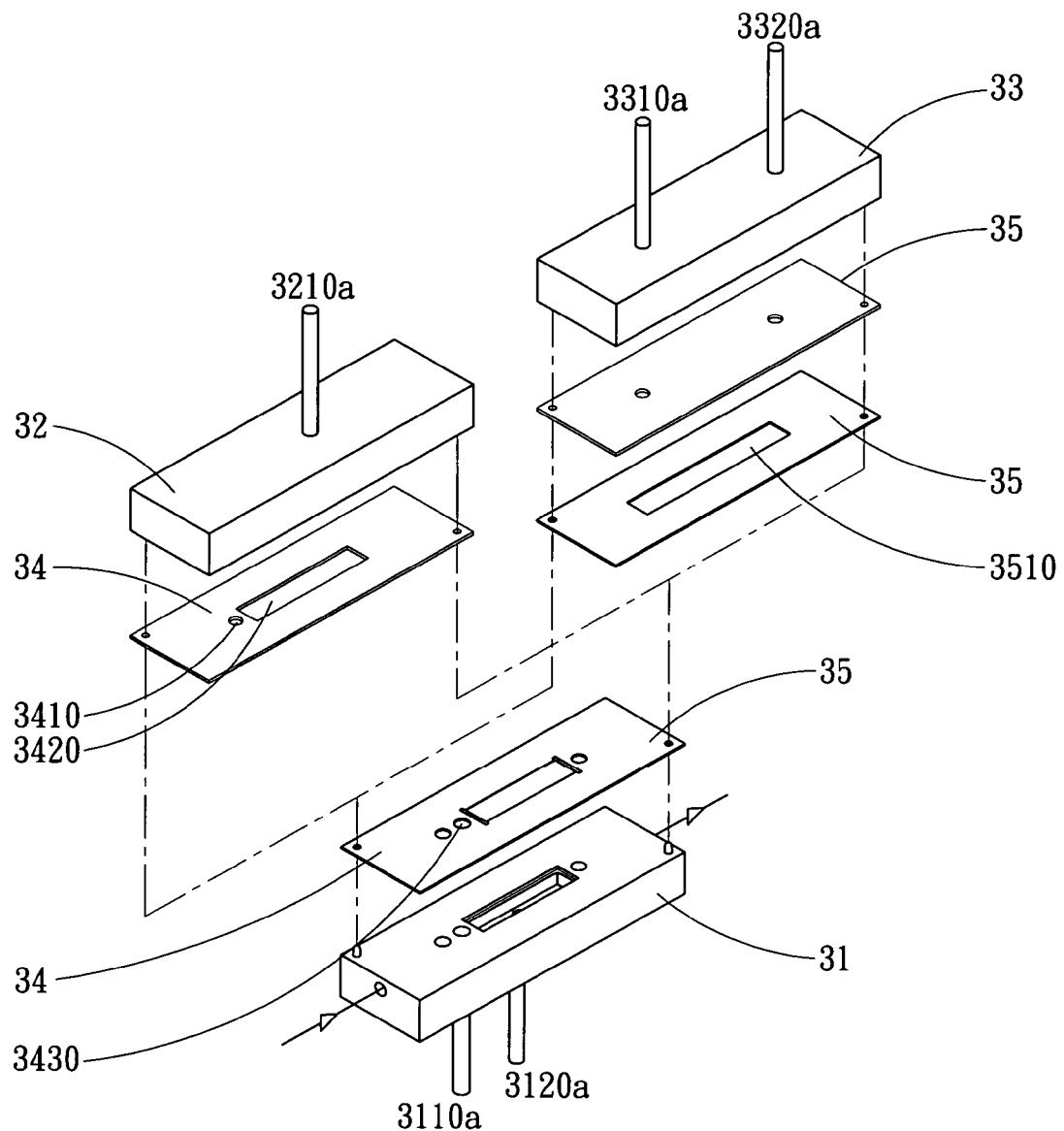
FIG. 3A to FIG. 3C are block diagrams illustrating a membrane potential measuring apparatus in accordance with a third preferred embodiment of the present invention.
Figure 3B:
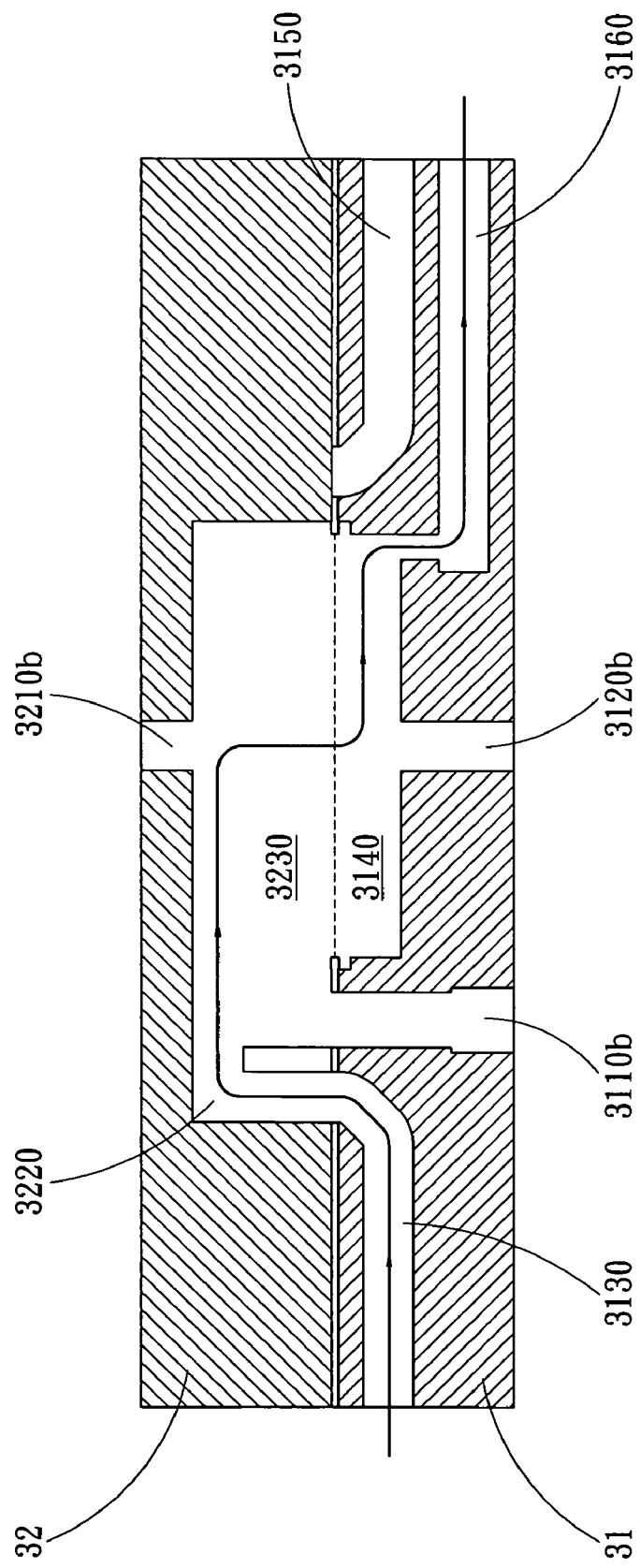
Figure 3C:
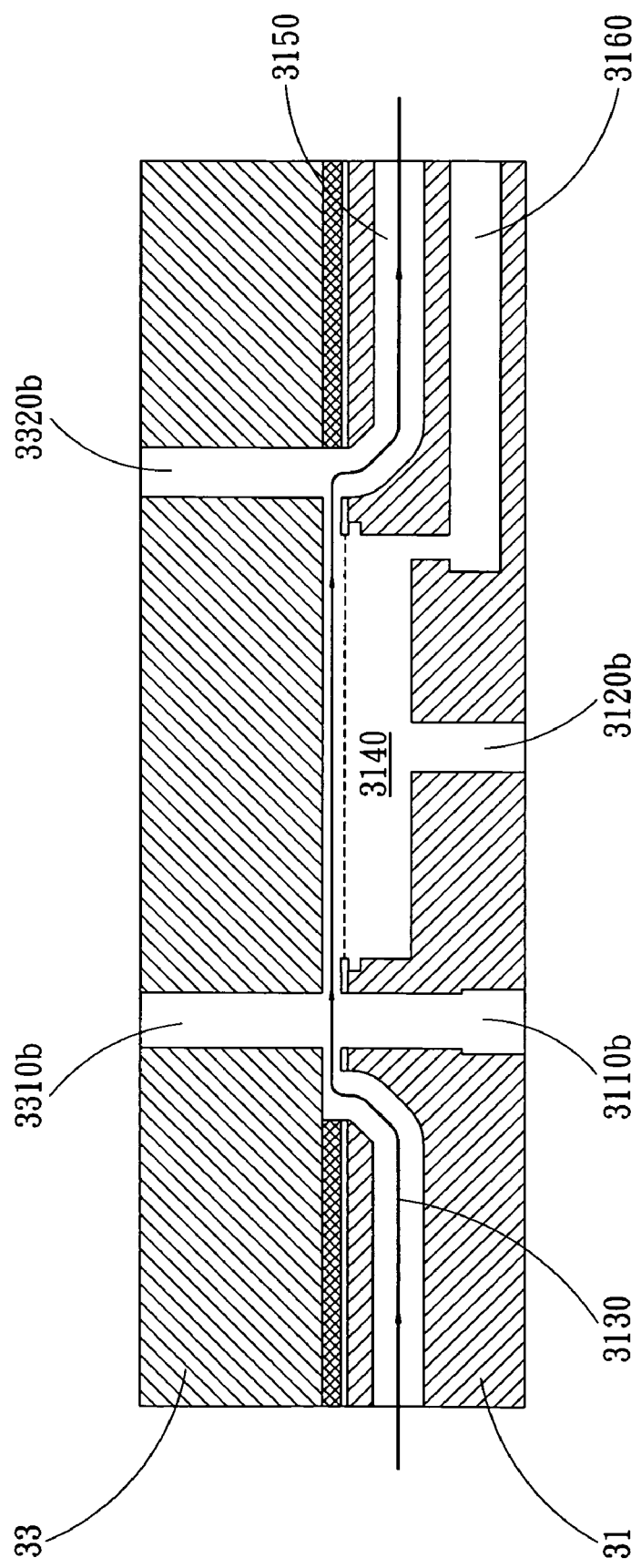
Figure 4A:
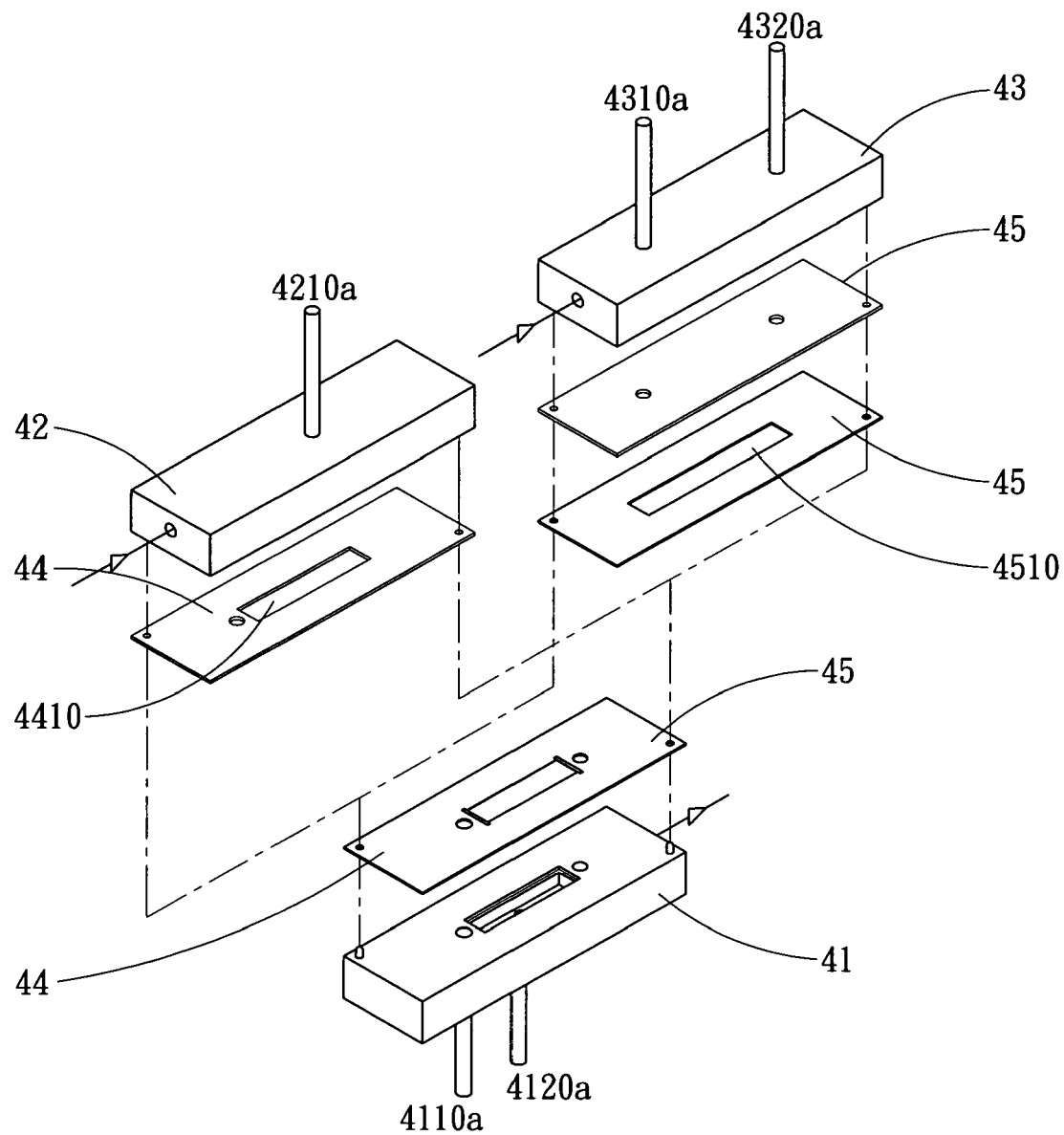
FIG. 4A to FIG. 4C are block diagrams illustrating a membrane zeta potential measuring apparatus in accordance with a fourth preferred embodiment of the present invention.
Figure 4B:
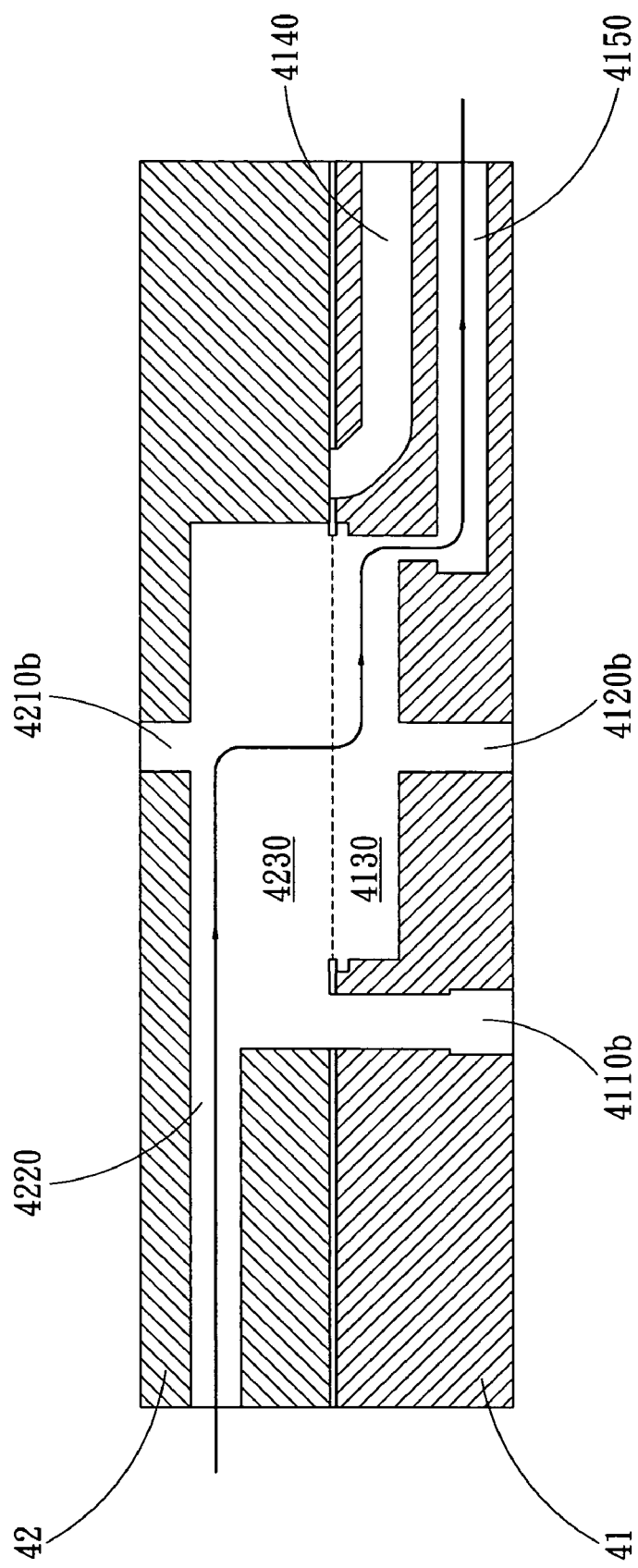
Figure 4C:
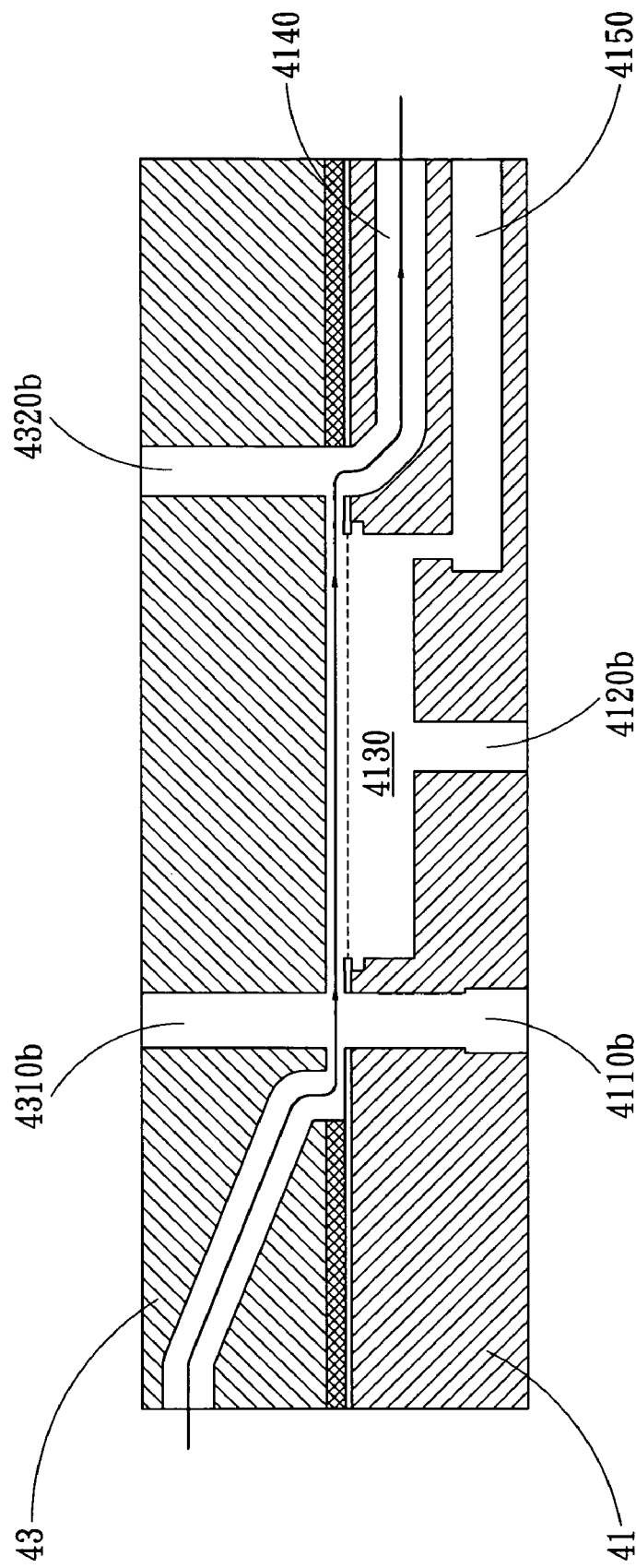
Figure 5A:
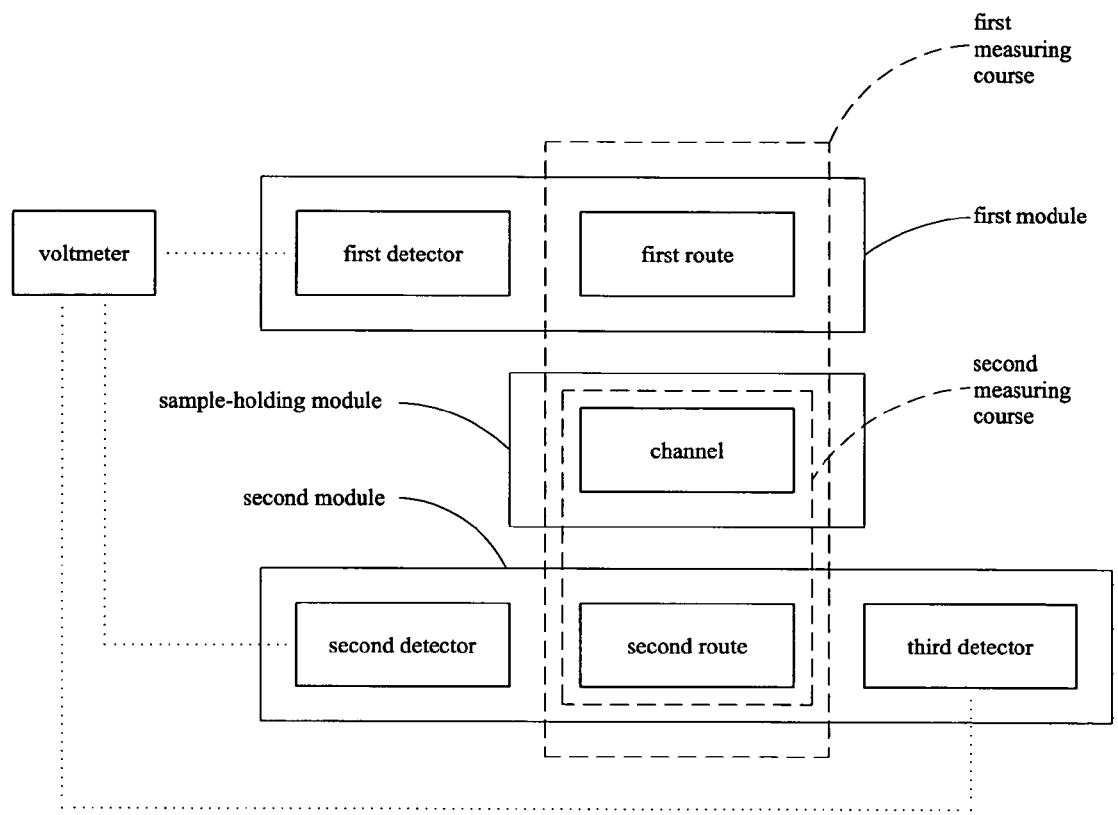
FIG. 5A is a block diagram illustrating a membrane zeta potential measuring system in accordance with a fifth preferred embodiment of the present invention.
Figure 5B:
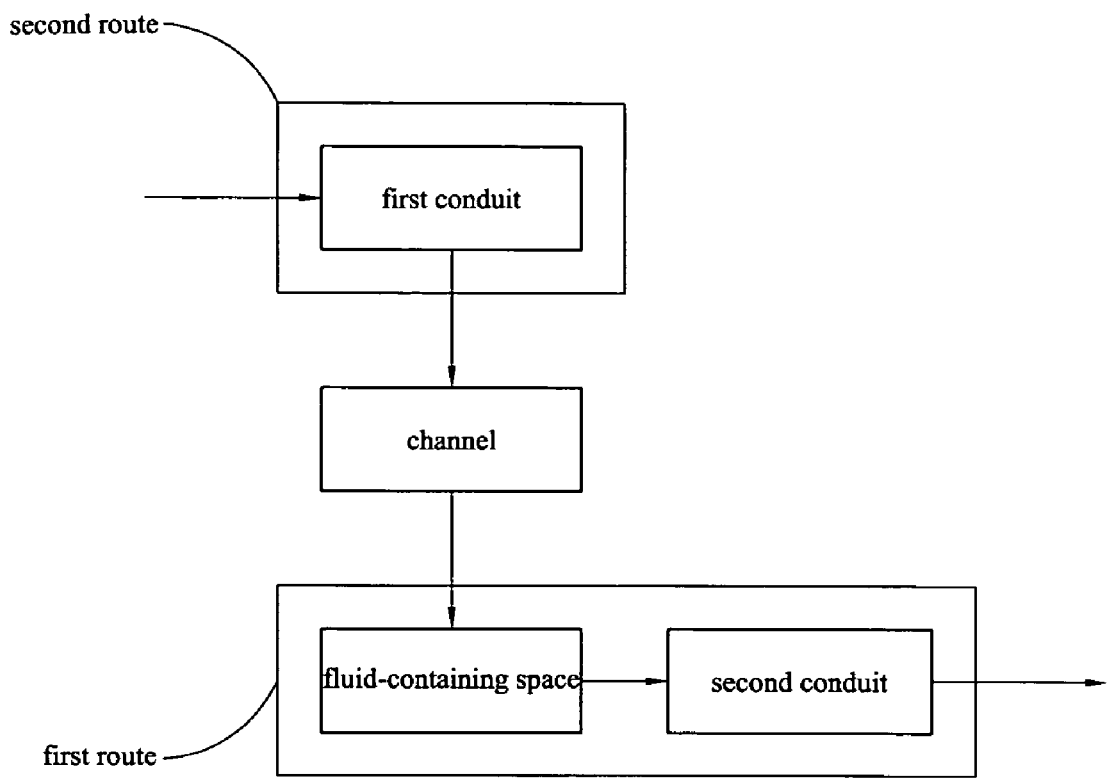
FIG. 5B is a block diagram illustrating the first measuring course of the membrane zeta potential measuring system in accordance with the fifth preferred embodiment of the present invention.
Figure 5C:
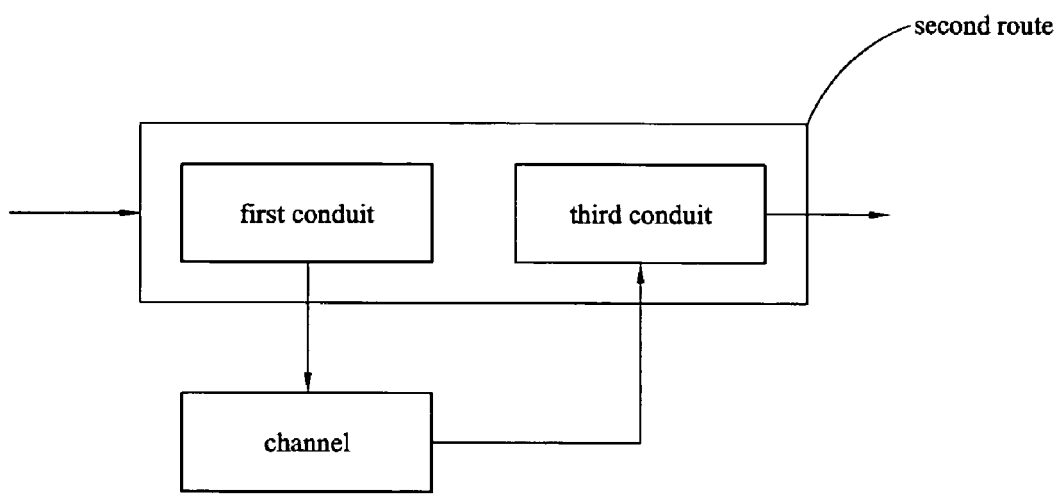
FIG. 5C is a block diagram illustrating the second measuring course of the membrane zeta potential measuring system in accordance with the fifth preferred embodiment of the present invention.
Figure 6:
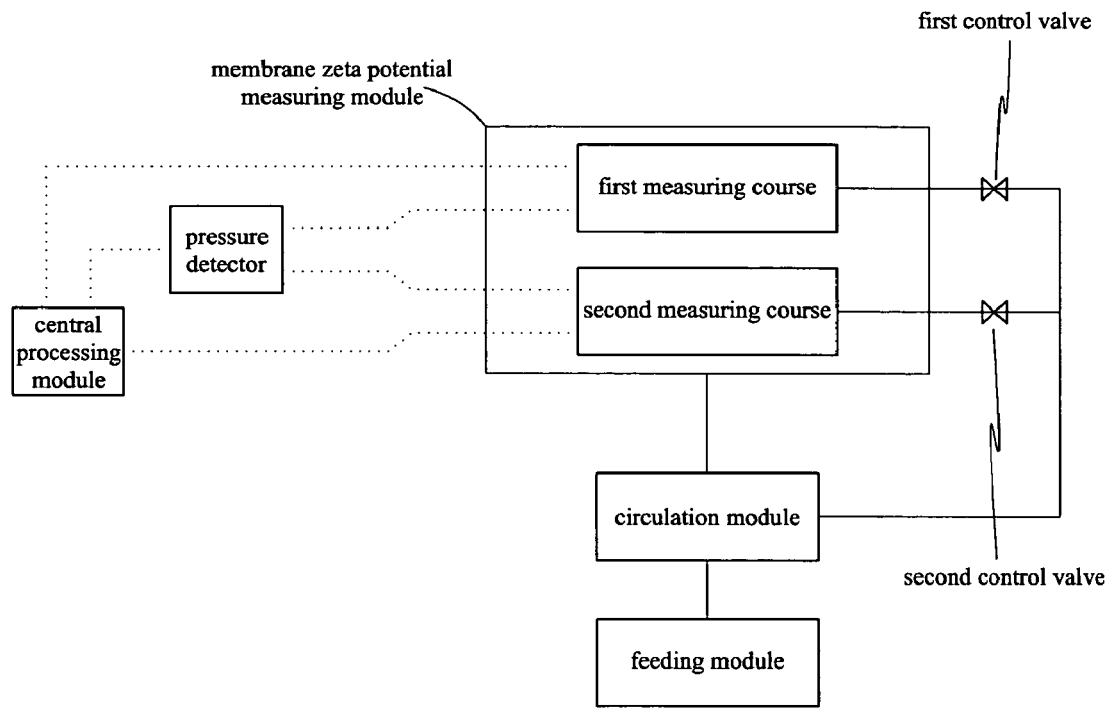
FIG. 6 is a block diagram illustrating a membrane zeta potential measuring system in accordance with a sixth preferred embodiment of the present invention.
Figure 7A:
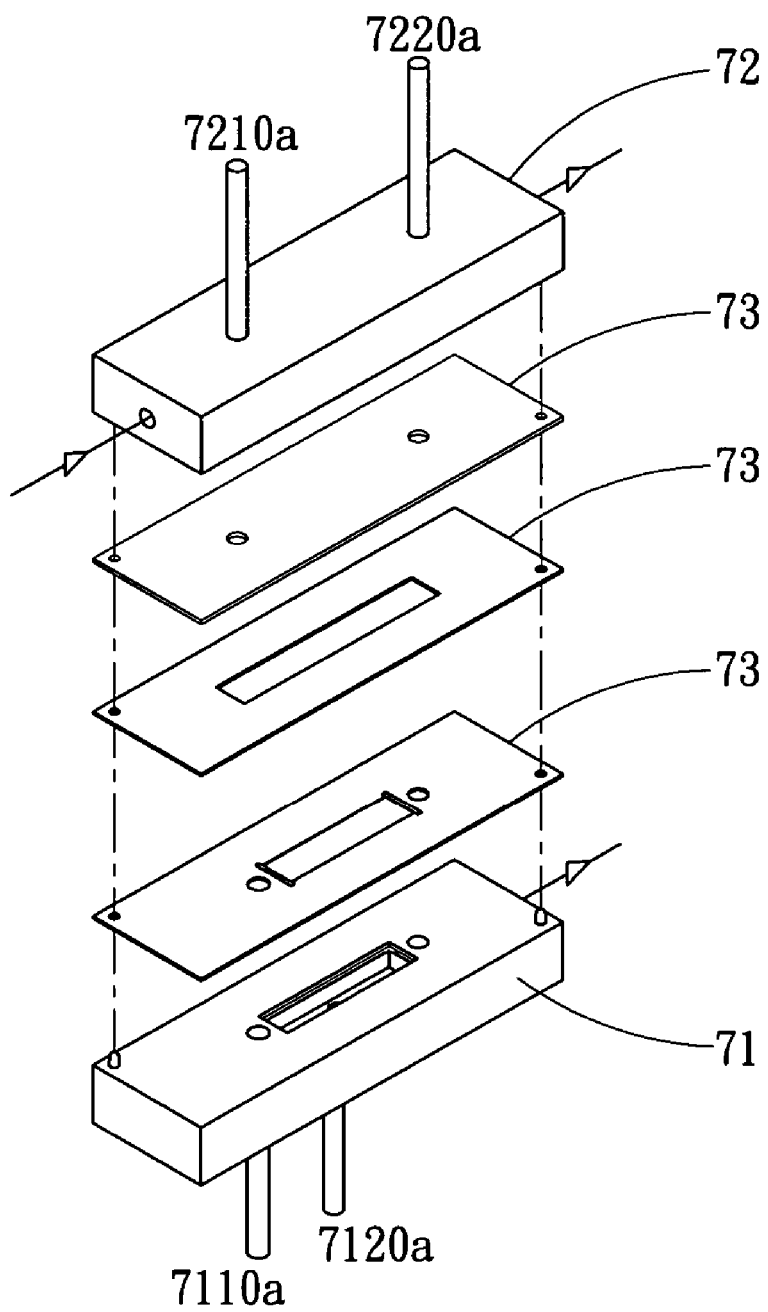
FIG. 7A to FIG. 7C are block diagrams illustrating a membrane zeta potential measuring apparatus in accordance with a seventh preferred embodiment of the present invention.
Figure 7B:
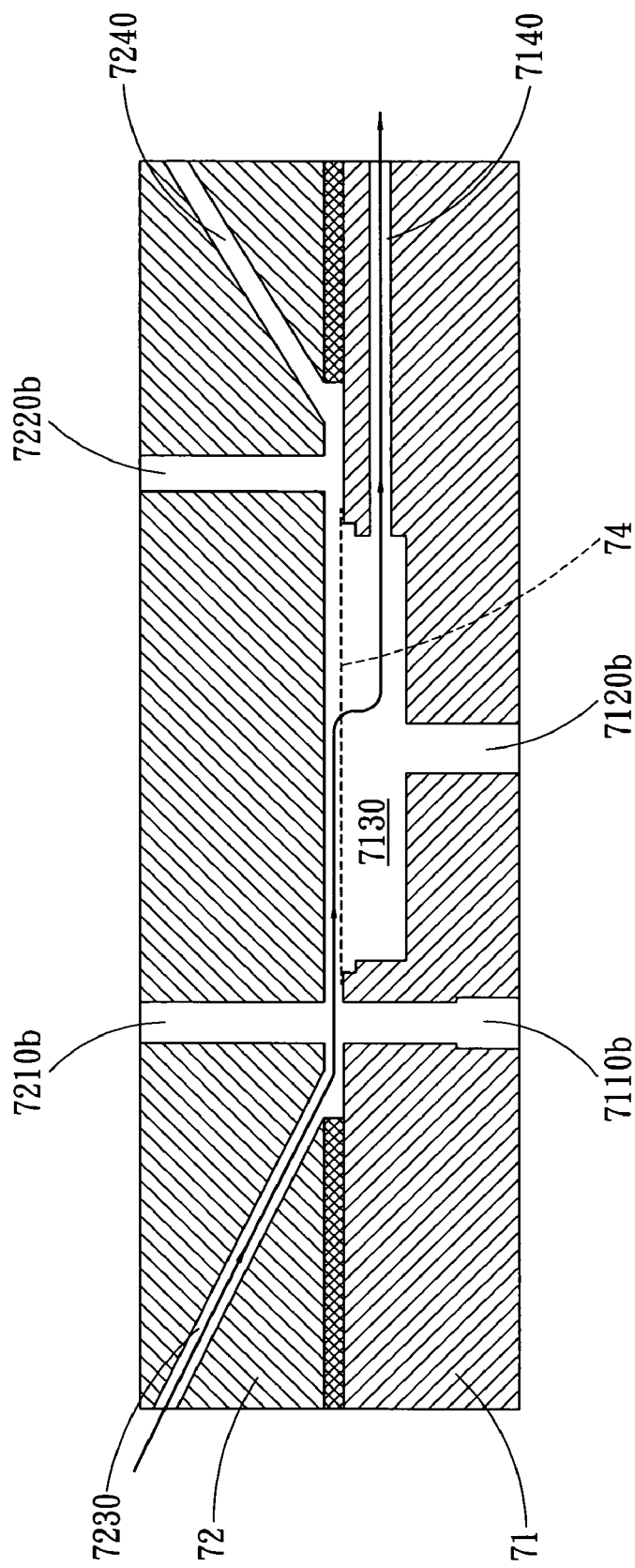
Figure 7C:
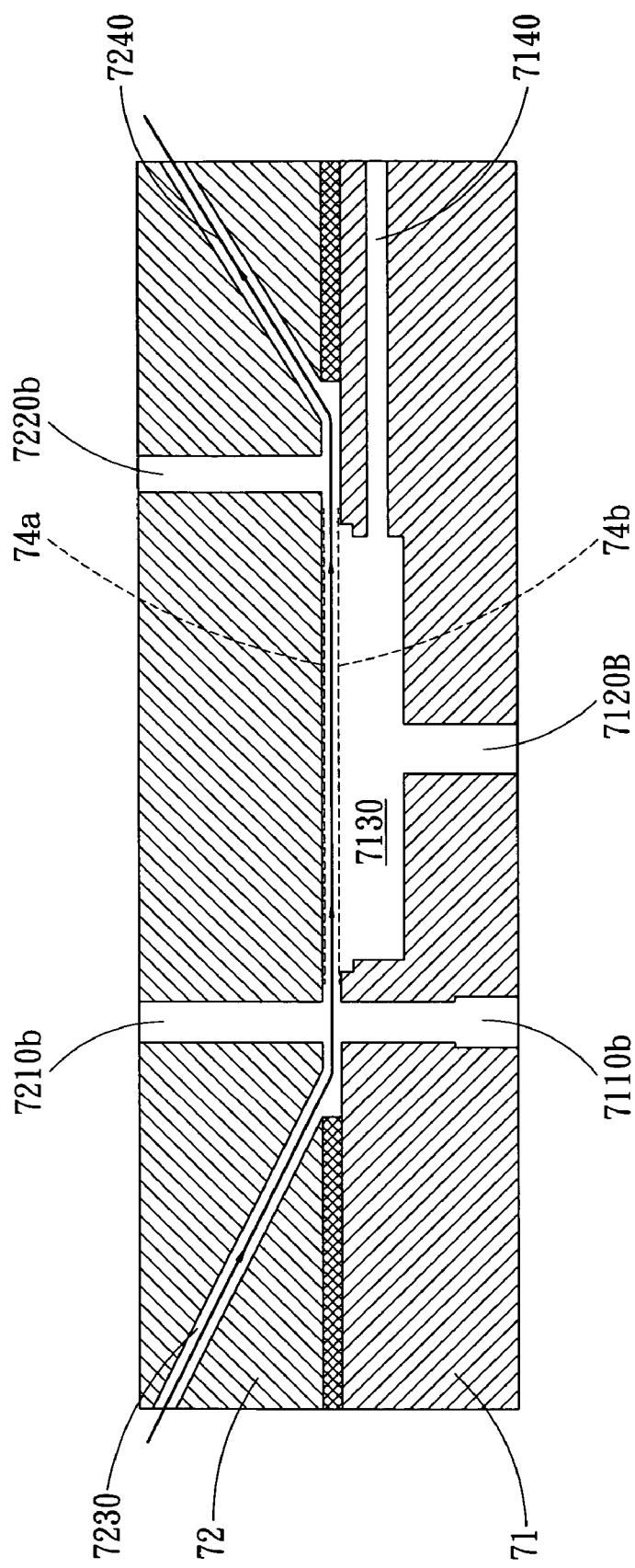

What is claimed is:

1. A membrane zeta potential measuring system, comprising: a first module having a first route and a first detector, wherein said first detector measures the potential of the fluid in said first route that has flowed through the pores of a membrane that is to be measured and generates a first potential signal; a second module having a second route and a second detector, wherein said second detector measures the potential of the fluid in said second route and generates a second potential signal; a first sample-holding module having a first channel, wherein said first sample-holding module is located between said first module and said second module and holds tight said membrane; a first measuring course to measure the zeta potential of the membrane pores, said first measuring course is formed by said first route, said first channel and said second route; a third module having a third detector and a fourth detector; a second sample-holding module having a second channel, wherein said second sample-holding module is located between said first module and said third module and holds tight two parallel membranes that are to be measured; a second measuring course to measure the zeta potential of the membrane surface, said second measuring course is formed by said first route and said second channel, said third detector measures the potential of the fluid at an inlet of said second channel and generates a third potential signal, said fourth detector measures the potential of the fluid at an outlet of said second channel and generates a fourth potential signal; and a voltmeter to receive said first and second potential signals to calculate a first potential drop from which the zeta potential of the pores of said membrane is then evaluated; similarly, said voltmeter receives said third and fourth potential signals to calculate a second potential drop from which the zeta potential of the surface of said membrane is then evaluated.

2. The membrane zeta potential measuring system in claim 1, wherein said first sample-holding module holds tight said membrane and places it in said first measuring course so the fluid can flow into the pores of said membrane.

3. The membrane zeta potential measuring system in claim 2, wherein said first sample-holding module comprises at least one holding device with a slot on it for the fluid to flow through, said holding device is used to apply pressure onto said membrane and make it to abut on said first module.

4. The membrane zeta potential measuring system in claim 3, wherein said at least one holding device consists of an elastic material.

5. The membrane zeta potential measuring system in claim 2, wherein said first sample-holding module further comprises at least one adjusting device to adjust the distance between said second module and said membrane so as to increase the fluid-containing space and uniform the internal pressure of the fluid.

6. The membrane zeta potential measuring system in claim 1, wherein said first measuring course comprises: a first conduit in said first route to lead the fluid into said membrane zeta potential measuring system; a first path in said first channel to receive the fluid from said first conduit; a second conduit in said second route to receive the fluid from said first path; a first fluid-containing space in said second route to receive the fluid from said second conduit and keep it for a while; a second path in said first channel to receive the fluid from said first fluid-containing space so the fluid in said second path can flow into the pores of said membrane; a second fluid-containing space in said first route to receive the fluid from the pores of said membrane; and a third conduit in said first route to receive the fluid from said second fluid-containing space and lead it out of said membrane zeta potential measuring system.

7. The membrane zeta potential measuring system in claim 6, wherein said second fluid-containing space comprises a porous board to support said membrane.

8. The membrane zeta potential measuring system in claim 1, wherein said second sample-holding module holds tight two parallel membranes that are to be measured in said second measuring course so the fluid can flow into the interspace between said two parallel membranes.

9. The membrane zeta potential measuring system in claim 8, wherein said second sample-holding module comprises at least one holding device with a slot on it for the fluid to flow through, said at least one holding device is used to apply pressure onto said two parallel membranes and make them to abut on said first module and said third module.

10. The membrane zeta potential measuring system in 9, wherein said at least one holding device consists of an elastic material.

11. The membrane zeta potential measuring system in claim 8, wherein said second sample-holding module further comprises at least one adjusting device to adjust the distance between said two parallel membranes.

12. The membrane zeta potential measuring system in claim 1, wherein said second measuring course comprises: a first conduit in said first route to lead the fluid into said membrane zeta potential measuring system; said second channel to receive the fluid from said first conduit and lead it into the interspace of said two parallel membranes; and a fourth conduit in said first route to receive the fluid from the interspace of said two parallel membranes and lead it out of said membrane zeta potential measuring system.

13. The membrane zeta potential measuring system in claim 1, further comprising a pressure detector to measure the internal pressure of the fluid in said second route located in said first measuring course.

14. The membrane zeta potential measuring system in claim 1, further comprising a pressure detector to measure the internal pressure of the fluid at the inlet of said second channel located in said second measuring course.

* * * * *